US010055906B1

(12) United States Patent
Fournier et al.

(10) Patent No.: US 10,055,906 B1
(45) Date of Patent: Aug. 21, 2018

(54) SYSTEM AND METHOD TO DETECT EMISSIONS OBD FALSE FAILURES

(71) Applicant: Opus Inspection, Inc., East Granby, CT (US)

(72) Inventors: Thomas J. Fournier, Tucson, AZ (US); Niranjan Vescio, Tucson, AZ (US); Peter M. McClintock, Marina Del Rey, CA (US)

(73) Assignee: Opus Inspection, Inc., East Granby, CT (US)

( * ) Notice: Subject to any disclaimer, the term of this patent is extended or adjusted under 35 U.S.C. 154(b) by 0 days.

(21) Appl. No.: 15/360,458

(22) Filed: Nov. 23, 2016

Related U.S. Application Data

(60) Provisional application No. 62/259,233, filed on Nov. 24, 2015.

(51) Int. Cl.
*G07C 5/08* (2006.01)
*G01M 15/10* (2006.01)
*F01N 11/00* (2006.01)

(52) U.S. Cl.
CPC ............ *G07C 5/0808* (2013.01); *F01N 11/00* (2013.01); *G01M 15/108* (2013.01); *G07C 5/0841* (2013.01)

(58) Field of Classification Search
USPC ........................................................ 701/29.3
See application file for complete search history.

(56) References Cited

U.S. PATENT DOCUMENTS

| | | | |
|---|---|---|---|
| 5,210,702 A | 5/1993 | Bishop et al. | |
| 5,726,450 A | 3/1998 | Peterson et al. | |
| 5,831,267 A | 11/1998 | Jack et al. | |
| 7,071,002 B1 * | 7/2006 | Tefft | G01M 15/102 422/83 |
| 7,073,320 B2 * | 7/2006 | Moritsugu | G01N 27/4175 123/688 |

(Continued)

OTHER PUBLICATIONS

Commonly assigned co-pending U.S. Appl. No. 15/342,764, filed Nov. 3, 2016, entitled System and Method to Detect Vehicle Emissions Noncompliance.

*Primary Examiner* — Tyler Paige
(74) *Attorney, Agent, or Firm* — Gardner, Linn, Burkhart & Ondersma, LLP

(57) ABSTRACT

A system and method to rapidly perform emissions measurements of in-use vehicles being driven by the general public for comparison with vehicle inspection OBD emission fault code testing results for determining if the inspection results indicate that false failures are being generated for a particular vehicle group, such as based on make and model, engine size, engine combustion management technology and/or pollution control technology, or determining if the inspection results correlate with increased in-use emissions. The system may access or integrate with a database of vehicle inspection OBD emission fault code testing results that may be analyzed to evaluate the existence of higher than normal or expected OBD failure rates for emissions related items. The system and method require no recruitment testing of in-use vehicles with potentially detectable connections, but instead incorporate a vehicle emissions remote sensing device that does not require mechanical or electrical connection to the vehicle.

21 Claims, 3 Drawing Sheets

(56) References Cited

U.S. PATENT DOCUMENTS

| | | | |
|---|---|---|---|
| 7,350,512 B1* | 4/2008 | Meacham | F02M 25/0809 |
| | | | 123/516 |
| 8,428,814 B2 | 4/2013 | Tripathi et al. | |
| 9,618,381 B1* | 4/2017 | Dudar | G01F 25/0069 |
| 2002/0092988 A1 | 7/2002 | Didomenico et al. | |
| 2006/0157001 A1* | 7/2006 | Rahman | F01P 11/14 |
| | | | 123/41.15 |
| 2007/0164220 A1 | 7/2007 | Luk | |
| 2008/0059019 A1* | 3/2008 | Delia | G07C 5/085 |
| | | | 701/33.4 |
| 2011/0137711 A1* | 6/2011 | Singh | G06Q 10/06 |
| | | | 705/7.38 |
| 2012/0152210 A1* | 6/2012 | Reddy | F02M 25/089 |
| | | | 123/520 |
| 2014/0069394 A1* | 3/2014 | Jentz | F02M 25/0809 |
| | | | 123/520 |
| 2014/0074385 A1* | 3/2014 | Dudar | F02M 25/0818 |
| | | | 701/113 |
| 2015/0114089 A1* | 4/2015 | Dudar | F02M 25/0809 |
| | | | 73/40 |

* cited by examiner

SYSTEM AND METHOD TO DETECT EMISSIONS OBD FALSE FAILURES

CROSS REFERENCE TO RELATED APPLICATION

The present application claims priority of U.S. provisional application Ser. No. 62/259,233 filed Nov. 24, 2015, by Opus Inspection, Inc. for SYSTEM AND METHOD TO DETECT EMISSIONS OBD FALSE FAILURES, which is hereby incorporated herein by reference in its entirety

BACKGROUND OF THE INVENTION

The present invention is directed to a system and method for determining whether the vehicle emission systems for particular vehicles, such as particular makes and models of vehicles, are falsely triggering on-board diagnostic ("OBD") codes during normal vehicle usage when the vehicles are properly operating within their associated regulatory standard.

Vehicle manufacturers are required to design and manufacture vehicles with self-report capabilities if the vehicle evaluates itself to be operating in a condition whereby its emissions exceed pre-determined limits associated with the regulatory standards under which the vehicle was initially approved, referred to as the type approval for the vehicle. This is accomplished via on-board computer processors that monitor vehicle systems and report results via OBD fault codes. The on board systems of the vehicles, however, do not measure emissions directly, but instead infer emissions performance across a broad array of operating conditions by way of complex software algorithms that process data related to on board sensors, such as oxygen and temperature sensors, catalytic convertor sensors, and the like.

Many governmental jurisdictions require owners to have their vehicles periodically inspected for compliance with emission control mandates, with such inspections being performed utilizing a vehicle's OBD system including to determine whether any emissions related OBD fault codes are triggered. Vehicles that do not meet the requirements may not qualify for registration until repairs are made, with the owners potentially subject to fines. Vehicle owners must subsequently have their vehicles repaired upon determining that OBD fault codes have been triggered. While vehicle manufacturers are required to repair emissions related failures under government-mandated emissions warranties, these warranties eventually expire and do not extend for the entire useful life of the vehicle.

SUMMARY OF THE INVENTION

The present invention provides a system and method to evaluate whether particular vehicle makes and models are improperly registering false positive OBD fault codes and thereby unnecessarily burdening vehicle owners with repairs by monitoring the actual emissions of vehicles to evaluate their in-use emissions performance, with the data being compared to emissions inspection history and associated OBD fault code data. The system and method may alternatively indicate or correlate a vehicle emissions non-compliance condition by correlating excessive emissions from in-use emissions performance with OBD fault code results.

According to an aspect of the present invention, a method of determining emissions OBD false failures includes evaluating vehicle inspection results to ascertain OBD emission fault codes for a vehicle group, such as to evaluate the existence of higher than normal or expected OBD failure rates for emissions related items for the vehicle group. The method further includes measuring the emissions of a plurality of vehicles using a vehicle emission remote sensing device during in-use operation of the vehicles to obtain in-use emission measurement results associated with the vehicle group in question. The in-use emission measurement results for the group are then evaluated to determine the presence of false failures in the vehicle inspection results.

In particular embodiments, the method comprises accessing one or more databases of vehicle inspection results, as well as comparing OBD emission fault code results for one vehicle group with OBD emission fault code results for another vehicle group to evaluate whether a particular group is exhibiting higher than normal or expected failure rates. The vehicle groups may be based on manufacturer, make and model, including for example, engine and model year or family of models with a common engine system or emissions system, or any combination thereof.

The remote sensing may comprise a light source for projecting a beam and a detector that receives the beam, with the beam projected across and/or onto a roadway and configured to pass through emissions of the vehicles. The remote sensing device may thereby rapidly measure one or more pollutants without being mechanically or electrically connected to the vehicles.

A camera may be employed to identify the vehicles by make and model, where the camera may be used to capture images of license plates for interfacing with a database of vehicle records. Additional identifiers may be determined, including the engine type, as well as engine combustion management technology and pollution control technology associated with the vehicle. Alternatively, the camera may be utilized with a vehicle recognition program to identify the make and model of the vehicle. Still further, the vehicle speed, acceleration, thermal warm-up status, and/or other operational parameters may be determined and used in the emissions measurement and analysis.

According to another aspect of the present invention, a system for determining OBD false failures comprises a database of vehicle inspection OBD emission fault code results for a plurality of tested vehicles, a vehicle emission remote sensing device operable to measure vehicle emissions of in-use vehicles passing thereby, a camera that captures images of vehicles for which emissions are measured to identify the in-use vehicles, and a sensor to detect operational parameters of the in-use vehicles for which emissions are measured. The system further includes a computer control operably integrated with the remote sensing device, sensor and camera, with the computer control being operable to evaluate the vehicle inspection results for a vehicle group and compare the in-use emission measurement results for vehicles corresponding to the vehicle group to determine the presence of false failures.

Vehicle manufacturers may become increasingly incentivized to ensure vehicles operate within emissions regulations, including to maintain the goodwill of their brand and avoid costly fines and penalties. As such, in order to avoid negative publicity or complaints, vehicle manufacturers may provide vehicles that tend to preemptively or aggressively inferentially indicate emissions issues by triggering OBD fault codes, such as based on overly stringent algorithms, prior to a vehicle actually operating outside of its regulatory standard type approval limits. These improperly triggered fault codes are referred to as false positives, and may increase with the age and/or mileage of the vehicle. Upon expiration of the vehicle warranties, vehicle owners are obligated to pay for vehicle emission services resulting from OBD detection of emission issues. Owner-paid emissions repairs may thus create an increasing economic concern that would tend to disproportionally apply to socioeconomic populations purchasing and/or driving older vehicles that are least able to afford such repairs, particularly as the useful life of vehicles increases. Accordingly, the present invention provides a system and method for evaluating and determining whether particular vehicles are unnecessarily generating emissions OBD false failures.

These and other objects, advantages, purposes and features of this invention will become apparent upon review of the following specification in conjunction with the drawings.

DESCRIPTION OF THE PREFERRED EMBODIMENTS

Figure 1:
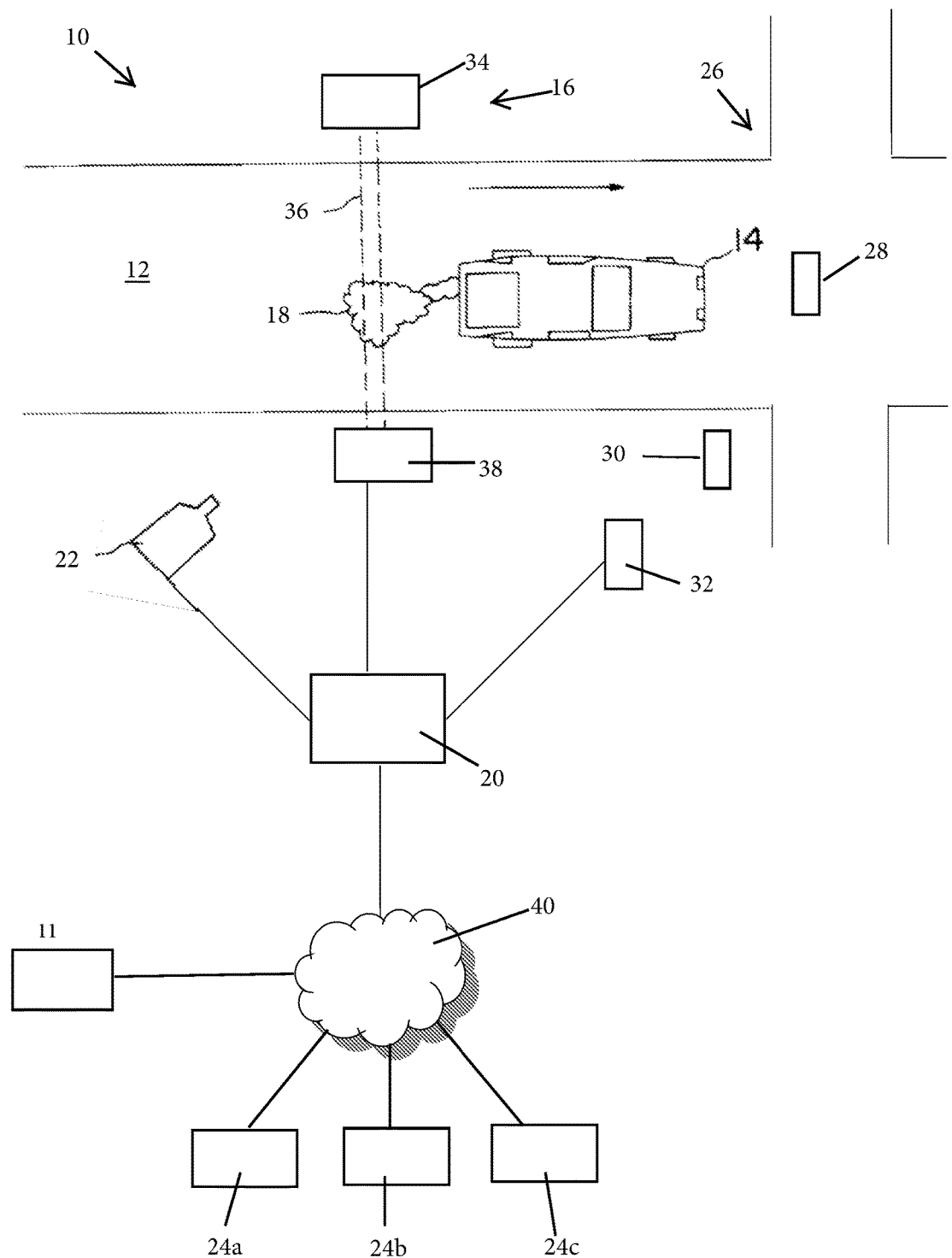
FIG. 1 is a schematic illustration of a system for detecting OBD false failures in accordance with an aspect of the present invention.

The present invention will now be described with reference to the accompanying figures, wherein the numbered elements in the following written description correspond to like-numbered elements in the figures. As understood from FIG. 1, a system 10 for detecting vehicle emissions OBD false failures is illustrated, with system 10 being integrated with or linked to a database 11 of established vehicle inspection results, such as may be performed by or on behalf of one or more governmental agencies pursuant to required periodic vehicle inspection. The database 11 thus includes OBD fault code data based on, for example, specific vehicle makes and models, including family of models with a common engine system, engine size, emissions control technologies, and/or other vehicle identification and emissions criteria. System 10 further incorporates or links with a database 24b of in-use vehicle emission analysis results, where the results are obtained by a vehicle emission remote sensing device (or "RSD") 16 that is operable to analyze and evaluate characteristics, constituencies or compositions of the exhaust plume or emissions 18 discharged by a vehicle 14 without mechanical or electrical connection to the vehicle.

System 10 is operable to analyze the OBD fault code data 11, including to evaluate whether particular vehicles, such as by make and model, or by other identification or groupings as discussed below, display higher than normal failure rates for emissions related systems and equipment. System 10 is additionally operable to analyze the actual in-use vehicle emissions results for particular correspondingly grouped vehicles, such as based on a particular make and model that exhibits above average OBD fault code failures. An indication that a particular identified vehicle, such as a particular make and model of vehicle, is generating potential false failures can thus be obtained if the actual in-use vehicle emissions results do not disclose higher actual emissions values correlating with the evaluated results of increased OBD fault code data from database 11. Regulatory authorities, vehicle manufacturers and/or consumer protection agencies may then be notified accordingly. System 10 may alternatively correlate actual higher emissions values from in-use vehicle emissions results with above average OBD fault code failures for a particular vehicle grouping, which may indicate a problem or concern with the vehicle grouping, such as based on make and model, being analyzed. In which case regulatory authorities, vehicle manufacturers and/or consumer protection agencies may be notified, including to instigate further emissions evaluations or studies of the subject vehicle grouping.

Figure 1A:
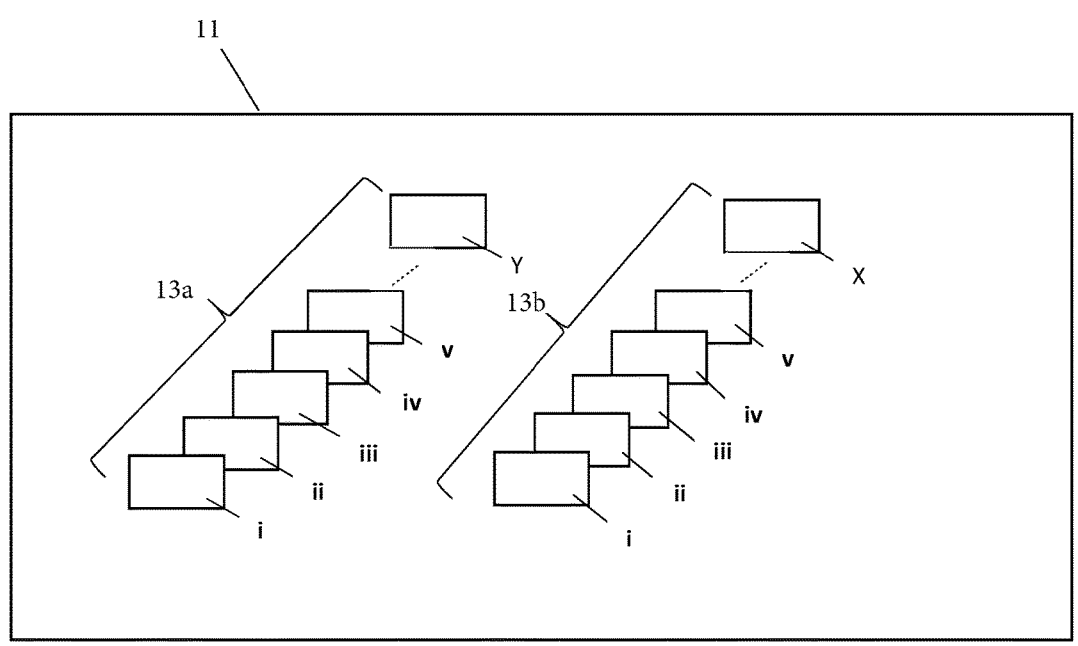
FIG. 1A is a schematic illustration of vehicle emissions inspection results based on make and model of a particular vehicle.

As noted, vehicle inspection results data 11 may be obtained during periodic vehicle inspections mandated by governmental jurisdictions. As understood from FIG. 1A, database 11 may include testing results 13a for Y samples of a particular vehicle grouping, such as by make and model vehicle, with it understood that similar results, such as 13b as well as others, for samples of other vehicle groupings are also ascertained. The data can thus include information regarding specific OBD fault codes that are triggered, such as based on particular systems or sensors, with the data including or correlated to information about the vehicle, such as based on various vehicle characteristics or commonalties of the vehicle. These groupings may include or be based on, for example, the manufacturer, make, model, engine and model year or family of models with a common engine system or emissions system, and including the vehicle year, mileage, engine size, engine combustion technologies or other vehicle identification and emissions criteria, or any combination thereof. For example, different brands of vehicles may share the same engine and emissions components whereby the present system may be employed to classify, group and compare related results together. Accordingly, it should be understood that reference herein to vehicle groupings and comparison of makes and models may encompass identifying and comparison of vehicles sharing common features for emissions evaluation purposes. Inspection results data 11 may include vehicle inspection results from additional sources other than mandated governmental periodic inspections, or may constitute inspection results from alternative sources other than such mandated periodic inspections. For example, inspection results data 11 may include or be data obtained from vehicle dealership or vehicle repair facilities, or the like.

In the illustrated embodiment, the vehicle emission RSD 16 is disclosed as being at least partially disposed adjacent roadway 12 over which vehicles travel, with RSD 16 being operable to analyze and evaluate characteristics, constituencies or compositions of the exhaust plume or emissions 18 discharged by vehicle 14. System 10 further includes a computing device or computer 20 integrated with RSD 16 for analyzing emissions 18, and a camera 22 that is operatively connected with computer 20 for capturing images of vehicle 14, with computer 20 being networked with various additional databases 24a, 24b, 24c, that may include information on vehicle regulatory standards, vehicle fuel economy ratings, and/or be used in the identification of vehicles.

In operation, system 10 determines operating parameters of the vehicle, such as its speed and acceleration, and analyzes emissions 18 via RSD 16 based on the operating parameters, as well as identifies the make and model of vehicle 14 via camera 22. This data is collected over time for numerous makes and models of vehicles during normal driving conditions, including for numerous samples of the same make and model, and including the same or equivalent vehicle years. Accordingly, emissions results and analysis can be performed without connecting vehicles to an emissions test device, and with actual driving conditions being analyzed.

In the illustrated embodiment, system 10 is shown as being further positioned proximate an intersection 26, where intersection 26 may include a traffic signal, such as a traffic light 28, a stop sign 30, or the like. Accordingly, RSD 22 is thus operable to evaluate emissions 18 during periods in which vehicle 14 undergoes non-steady state operation, such as when vehicle 14 is accelerating. Alternatively, system 10 may be positioned proximate an on-ramp, such as for a freeway, or highway, or other high-speed vehicular traffic roadway. Analysis of emissions 18 may thus be conducted of emissions 18 that are generated during prolonged high-load, vehicle acceleration.

System 10 is therefore shown in the illustrated embodiment to include a sensor 32, where sensor may comprise a vehicle speed sensor, such as a radar and/or laser type sensor. Sensor 32 is shown as being operatively connected with computer 20, where sensor 32 may additionally provide time data for determination of acceleration or provide acceleration data directly, or computer 20 may itself make acceleration determinations based simply on received velocity data. The driving mode of vehicle 14 may thus be determined, where the driving mode impacts vehicle emissions and can be taken into consideration during data analysis of the emissions testing results.

As noted, RSD 16 is constructed to be an apparatus for remote analysis or measurement of vehicle emissions or exhaust gas, and may be constructed as a conventional vehicle emission remote sensing device. In the illustrated embodiment, RSD 16 includes a light source 34 that projects a beam 36, with beam 36 aligned to pass through exhaust emissions plume 18. Although beam 36 is illustrated as extending across roadway 12, it should be appreciated that alternative configurations may be employed, including where a beam is projected onto the roadway rather than across the roadway. Light source 34 may supply infrared ("IR") radiation, with source 34 comprising a broad band IR source, and/or may supply ultraviolet ("UV") radiation. The passage of the beam 36 through the exhaust gas plume 18 results in the selective partial absorption of various wavelengths within the broad band beam, the selective absorption occurring because of the presence of $NO_x$, water vapor, $CO_2$, CO, HC (hydrocarbons), and other species within the exhaust gas. As is known by those of skill in the art, each of the aforementioned species absorbs infrared radiation at or near a known wavelength or wavelengths. RSD 16 thus comprises a fast emissions analyzer that is neither mechanically nor electrically connected to the vehicle 14 undergoing emissions measurement and analysis.

After passing through the plume 18, the beam 36 passes into a receiver or detector 38, where the detector 38 may include a beam integrator or diffuser. The diffused beam is subsequently applied to a plurality of narrow band filters, each of the filters corresponding to a measurement channel. Each filter is selected so as to pass a predetermined narrow band of wavelengths to a focal plane having a plurality of photodetectors individually tuned for a specific pollutant. Each photodetector outputs an electrical signal to an input of a corresponding measurement channel, and may include suitable analog electronics and an analog-to-digital converter.

There can be, for example, numerous spectral measurement channels, depending upon the number of pollutants and reference channels that are desired to be monitored. For example, there can be an NO spectral channel (having a filter with a pass band centered on about 5.26 micrometers), an $H_2O$ spectral channel (having a filter with a pass band centered on about 5.02 micrometers), a first reference, or $CO_2$, spectral channel (having a filter with a pass band centered on about 4.2 micrometers), a CO spectral channel (having a filter with a pass band centered on about 4.6 micrometers), an HC spectral channel (having a filter with a pass band centered on about 3.3 micrometers), and a second reference spectral channel having a filter with a pass band centered on about 3.8 micrometers. Additional channels to measure other pollutants can also be added if desired.

Computer 20 is integrated with RSD 16 and operable to provide the required signal processing of the outputs of detector 38. A vehicle emission remote sensing device employed in the present invention may thus be constructed as disclosed in either of U.S. Pat. No. 5,210,702 or U.S. Pat. No. 5,831,267, which are both hereby incorporated herein by reference in their entireties.

In addition to the speed/acceleration of vehicle 14, system 10 may obtain and evaluate additional information regarding operating parameters of vehicle 14. For example, computer 20 may receive information regarding the thermal warm-up status of vehicle 14, such as by way of wireless temperature or thermal sensors, such as infrared temperature sensors, or the like. Such a sensor may be separately located or incorporated into sensor 32, where sensor 32 may thus comprise various instruments for obtaining differing data. Accordingly, RSD 16 may additionally consider the thermal warm-up state of vehicle 14 during analysis of the emissions 18 of the vehicle 14. Still further, additional operational parameters may be determined and used in evaluating the vehicle emissions, including the vehicle load, and including the ambient weather conditions during evaluation.

In the illustrated embodiment, and as previously noted, computer 20 is further operatively connected with camera 22 and one or more databases, such as illustrated databases 24a, 24b and 24c, which may comprise separate computing devices or networks that are operatively connected with computer 20, such as by a network or internet 40. Camera 22 is used to capture images of vehicle 14 for the purpose of identifying the make and model of vehicle 14. It should be understood that the identification of the vehicles may be based on or according to various vehicle characteristics or commonalities. This includes, for example, the manufacturer, make, model, engine and model year or family of models with a common engine system or emissions system, or any combination thereof. Accordingly, it should be understood that reference herein to identifying vehicles and comparison of makes and models may encompass identifying and comparison of vehicles sharing common features for emissions evaluation purposes, including without limitation engine size, engine combustion technology and emissions systems. Comparisons may then be made between the identified vehicles from the in-use operation measurements relative to the vehicle groupings based on periodic testing, as discussed below.

Camera 22, for example, may be used to capture an image of the license plate of vehicle 14 with computer 20 configured to access and retrieve or receive information based thereon from database 24a, where database 24a may comprise a vehicle database of vehicle registration data from secretary of state records, records of a state department of motor vehicles, or other such data from a governmental or regulatory body or the like. System 10 may additionally include or incorporate a governmental or other database containing vehicle fuel economy data and standards. Alternatively or additionally, camera 22 and/or computer 20 may incorporate a vehicle or object recognition program or software for determining a vehicle make and model without the need to access governmental records, where such a program is operable to directly or indirectly, such as via a database lookup, determine the vehicle make and model. The obtained data or ascertained information may further include vehicle engine size information, combustion management technology of the vehicle, and/or pollution control information of the vehicle. Still further, accessed data, such as from a governmental body, may further include information regarding the emissions inspection history of the particular vehicle. The vehicle inspection history information may be used, for example, to confirm that the particular vehicle under evaluation is considered to be a normally operating and configured representative example of the particular make and model.

In the illustrated embodiment, system 10 is additionally configured to record results of vehicle emissions analysis performed by RSD 16 for each vehicle so evaluated, with the data recorded in database 24b. The data may be recorded as noted above, for example, based on particulars related to vehicle make and model or other characteristics. Accordingly, system 10 is able to analyze emissions 18 from vehicles 14 that pass by on roadway 12, such as during acceleration on an on-ramp. It should be appreciated that system 10 is operable to obtain significant data collection on particular groups or types of vehicles as the vehicles pass by system 10 during normal operating conditions. The acquired data may then be analyzed to obtain emissions information directed to a particular make and model of vehicle based on the population of such vehicles for which RSD 16 has analyzed emissions. In operation, system 10 may be located at a particular intersection 26 through which the same vehicle may travel multiple times. Accordingly, system 10 may account for this by limiting the subsequent data analysis to the emissions analysis results of unique vehicles.

Figure 2:
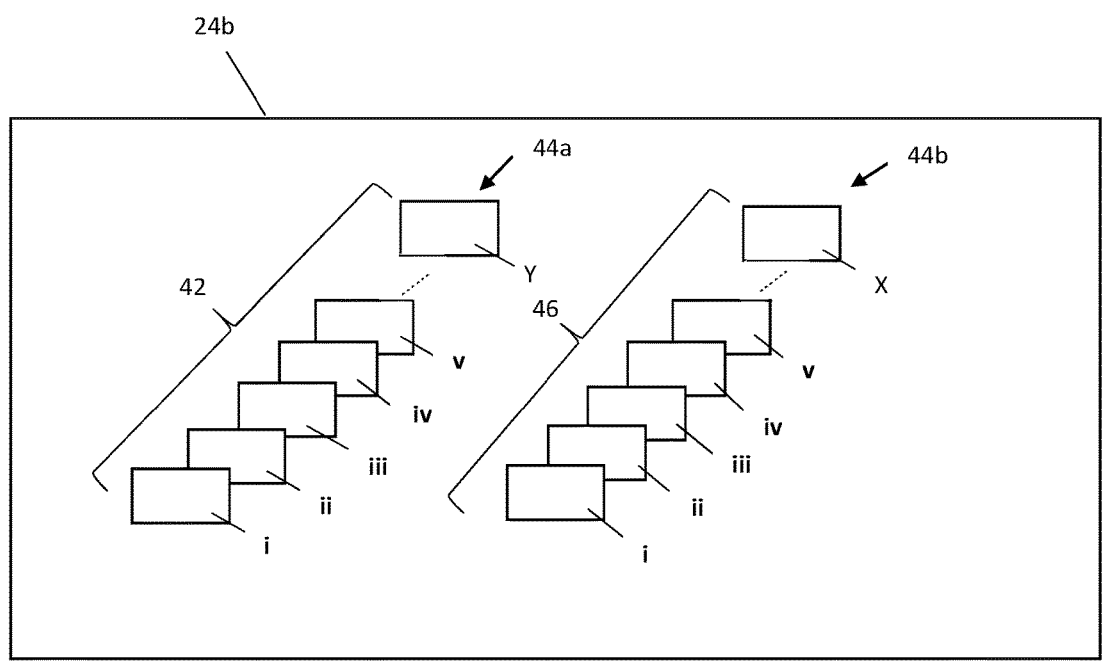
FIG. 2 is a schematic illustration of vehicle emissions analysis results for different versions of particular makes and models of vehicles that are determined and recorded by the system of FIG. 1 for performing data analysis.

As understood from FIG. 2, various emissions analysis results 42 for a particular vehicle make and model 44a are recorded in database 24b, where results 42 are obtained for Y different examples of the particular make and model 44a. Similarly, results 46 corresponding to a different vehicle make and model 44b are recorded in database 24b, where results 46 are obtained for X different examples of the particular make and model 44b. It should be readily appreciated that emissions data for numerous different types of makes and models of vehicles can be readily obtained by locating system 10 at roadway 12. Moreover, results may be recorded for different driving modes and/or parameters. For example, results may be obtained, determined, and recorded during vehicle acceleration, at a constant velocity of the vehicle, during vehicle warm-up state, or the like.

Still further, system 10 may access or receive data regarding the regulatory standards under which an identified vehicle 14 was certified for its emissions output based on the particular identified make and model of the vehicle 14. For example, computer 20 may access database 24c, with database 24c comprising a standards database containing data information and records regarding the emissions testing results pursuant to regulatory standards testing and/or regulatory standards requirements.

As noted above, system 10 analyzes OBD fault code results 13 for various makes and models, including based on various parameters such as engine size, emissions control technologies, model year, mileage, and the like. Statistical analysis may be performed to evaluate if the OBD fault codes exhibited for a particular vehicle grouping are higher than normal or expected, such as based on comparisons to other similar classes or platforms of vehicles produced by the same or other manufacturers. This may include, for example, comparisons of mid-sized sedans, economy cars, sport utility vehicles, trucks, and the like.

Actual vehicle emissions analysis results, such as results 42 or 44, may correspondingly be analyzed and evaluated, such as for a particular vehicle make or model that has been determined to be exhibiting higher than normal OBD fault codes. An indication that a particular make and model of vehicle is generating potential false failures can thus be obtained if the actual in-use vehicle emissions results do not disclose higher actual emissions values correlating with the evaluated results of increased OBD fault code data from database 11, including if the actual in-use vehicle emissions results indicate the vehicle to be operating within its regulatory type approval emissions certification.

Regulatory authorities, vehicle manufacturers and/or consumer protection agencies may then be notified accordingly to alleviate the assessment of unwarranted vehicle repairs against vehicles that generate false OBD fault code failures.

Alternatively, system 10 may determine that a particular vehicle grouping exhibits actual higher emissions values from in-use vehicle emissions results, and correlate such results with above average OBD fault code failures for the vehicle grouping. This may indicate a problem or concern with the particular vehicle grouping, such as based on make and model, being analyzed. That is, the OBD fault codes do not disclose false failures, but instead correlate to vehicles that are potentially operating out of compliance with emissions standards. In which case regulatory authorities, vehicle manufacturers and/or consumer protection agencies may be notified, including to instigate further emissions evaluations or studies of the subject vehicle grouping, such as by use of a portable emissions monitoring system or other testing procedures It should be appreciated that numerous alternatives to system 10 may be employed within the scope of the present invention. For example, although system 10 is disclosed in connection with a computer 20 that is generally local to roadway 12, an alternative computer may be employed in which information is transmitted over a network, such as network 40, for remote data processing. Moreover, more than one computer may be employed in system 10. Still further, alternative databases and/or numbers of databases may be used for storing and/or retrieving information, including utilizing data information locally stored on a computer rather than employing remote databases.

Moreover, other changes and modifications in the specifically described embodiments can be carried out without departing from the principles of the present invention which is intended to be limited only by the scope of the appended claims, as interpreted according to the principles of patent law including the doctrine of equivalents.

The embodiments of the invention in which an exclusive property or privilege is claimed are defined as follows:

1. A method of determining emissions on-board diagnostic ("OBD") false failures comprising:
    evaluating vehicle inspection results for a plurality of tested vehicles in an electronic database to ascertain on-board diagnostic ("OBD") emission fault codes for a vehicle group;
    measuring the emissions of a plurality of vehicles using a vehicle emission remote sensing device during in-use operation of the vehicles to obtain in-use emission measurement results, wherein the remote sensing device is positioned at least partially at or adjacent a vehicle roadway over which the vehicles travel;

identifying the vehicles for which in-use emissions are measured using a camera operatively positioned with said remote sensing device, said camera being operable to capture images of vehicles for which emissions are measured by said remote sensing device to identify the in-use vehicles; and evaluating in-use emission measurement results with a computer for vehicles corresponding to the vehicle group to determine the presence of false failures in the vehicle inspection results for the vehicle group.

2. The method of claim 1, wherein said evaluating vehicle inspection results comprises accessing one or more databases of vehicle inspection results.

3. The method of claim 2, wherein said evaluating vehicle inspection results comprises ascertaining OBD emission fault codes for two vehicle groups and comparing OBD emission fault code results for one of the vehicle groups with OBD emission fault code results for the other vehicle group, and wherein said evaluating in-use emission measurement results comprises evaluating in-use emission measurement results for vehicles corresponding to at least one of the two vehicle groups to determine the presence of false failures in the vehicle inspection results for the said at least one of the two vehicle groups.

4. The method of claim 3, wherein said evaluating vehicle inspection results comprises evaluating OBD fault code failure rates.

5. The method of claim 3, wherein said evaluating in-use emission measurement results comprises evaluating in-use emission measurement results for vehicles corresponding to both of the two vehicle groups to determine the presence of false failures in the vehicle inspection results for at least one of the two vehicle groups.

6. The method of claim 1, wherein a vehicle group comprises vehicles that are related based on at least one of vehicle make and model, model year, engine size, or emissions equipment.

7. The method of claim 1, wherein the remote sensing device comprises a light source for projecting a beam and a detector that receives the beam, and wherein the remote sensing device is disposed adjacent a roadway with the beam being projected across and/or onto the roadway and configured to pass through emissions of the vehicles.

8. The method of claim 1, wherein said measuring the emissions of a plurality of vehicles comprises measuring selected pollutants of the emissions.

9. The method of claim 1, wherein said camera captures images of vehicle license plates and said method further comprises accessing a vehicle database to identify the vehicle by its license plate.

10. The method of claim 1, wherein said camera captures images of the vehicles and the vehicles are identified via an object recognition program.

11. The method of claim 1, wherein said measuring the emissions of a plurality of vehicles further includes sensing an operational parameter of the vehicles during in-use operation of the vehicles.

12. The method of claim 11, wherein said sensing an operational parameter of the vehicles includes sensing the speed, acceleration, and/or thermal-warm up state of the vehicles.

13. The method of claim 1, wherein said comparing in-use emission measurement results for vehicles corresponding to said vehicle group to evaluate the presence of false failures further comprises comparing in-use emission measurement results to regulatory emissions standards associated with said vehicle group.

14. A system for determining emissions on-board diagnostic ("OBD") false failures comprising:

a database of vehicle inspection OBD emission fault code results for a plurality of tested vehicles;

a vehicle emission remote sensing device, said remote sensing device operable to measure vehicle emissions and configured to be positioned adjacent a roadway for measuring the emissions of a plurality of in-use vehicles passing thereby;

a computer control, said computer control operably integrated with said remote sensing device;

a camera, said camera being operable to capture images of vehicles for which emissions are measured by said remote sensing device to identify the in-use vehicles, with said camera being operably connected with said computer control and configured to being positioned adjacent the roadway with said remote sensing device;

a sensor, said sensor being operable to detect operational parameters of the in-use vehicles for which emissions are measured by said remote sensing device with said sensor being operably connected with said computer control and configured to being positioned adjacent the roadway with said remote sensing device, wherein the operational parameters include the speed and/or acceleration of the vehicles;

said computer control being operable to evaluate the vehicle inspection results for a vehicle group and compare the in-use emission measurement results for vehicles corresponding to said vehicle group to determine the presence of false failures.

15. The system of claim 14, wherein said remote sensing device comprises a light source for projecting a beam and a detector that receives the beam, and wherein said remote sensing device is configured to be disposed adjacent the roadway with the beam being projected across and/or onto the roadway and configured to pass through emissions of the vehicles.

16. The system of claim 14, wherein said camera is operable to capture images of the license plates of the vehicles, and wherein said computer control is operably connected with a vehicle database for identifying the vehicle by its license plate.

17. The system of claim 14, further including a vehicle recognition program, and wherein said camera is operable to capture images of the vehicle with said vehicle recognition program being operable to identify the vehicle.

18. The system of claim 14, wherein said sensor is operable to detect the thermal warm-up status of the vehicles.

19. The system of claim 14, wherein said computer control comprises a plurality of computer devices.

20. The system of claim 14, wherein said sensor includes a radar and/or a laser for determining vehicle speed and/or acceleration.

21. The system of claim 14, wherein said computer control comprises a first computer operative to control said remote sensing device and a second computer for data processing to evaluate the vehicle inspection results for a vehicle group and compare the in-use emission measurement results for vehicles corresponding to said vehicle group to determine the presence of false failures.

* * * * *